United States Patent
Dodinet et al.

(10) Patent No.: US 11,717,476 B2
(45) Date of Patent: Aug. 8, 2023

(54) *MORINGA PEREGRINA* SEED EXTRACT RICH IN 2,5-DIFORMYLFURAN, PROCESS FOR OBTAINING SAME AND USE THEREOF IN COSMETIC COMPOSITIONS

(71) Applicant: AGENCE FRANAISE POUR LE DEVELOPPEMENT D'AL ULA, Paris (FR)

(72) Inventors: Elizabeth Dodinet, Saint-Laurent d'Olt (FR); Vincent Bourgeteau, Ferel (FR)

(73) Assignee: AGENCE FRANAISE POUR LE DEVELOPPEMENT D'AL ULA, Paris (FR)

( * ) Notice: Subject to any disclaimer, the term of this patent is extended or adjusted under 35 U.S.C. 154(b) by 0 days.

(21) Appl. No.: 17/633,380

(22) PCT Filed: May 21, 2021

(86) PCT No.: PCT/EP2021/063690
§ 371 (c)(1),
(2) Date: Feb. 7, 2022

(87) PCT Pub. No.: WO2021/234159
PCT Pub. Date: Nov. 25, 2021

(65) Prior Publication Data
US 2023/0133310 A1 May 4, 2023

(30) Foreign Application Priority Data

May 21, 2020 (FR) ........................ 2005429
Mar. 17, 2021 (FR) ........................ 2102686

(51) Int. Cl.
*A61K 36/00* (2006.01)
*A61K 8/9789* (2017.01)
*A61K 8/49* (2006.01)
*A61Q 19/08* (2006.01)

(52) U.S. Cl.
CPC .......... *A61K 8/9789* (2017.08); *A61K 8/4973* (2013.01); *A61Q 19/08* (2013.01); *A61K 2800/522* (2013.01); *A61K 2800/782* (2013.01)

(58) Field of Classification Search
CPC .................................................. A61Q 19/08
See application file for complete search history.

(56) References Cited

FOREIGN PATENT DOCUMENTS

FR 2776519 A1 10/1999
FR 2946879 A1 12/2010

OTHER PUBLICATIONS

Mahmoud A. Koheil et al. "Anti-inflammatory and antioxidant activities of Moringa peregrina Seeds"; Free Radicals and Antioxidants, vol. 1, No. 2, Apr. 1, 2011 (Apr. 1, 2011), pp. 49-61; DOI: 10.5530/ax.201 I.2.10; ISSN: 2231-2536, XP055753955.
Sha Ymaa Fadhel Abbas Alba et al. "Cytotoxic and Urease Inhibition Potential of Moringa peregrina Seed Ethanolic Extract"; International Journal of Pharmacology, PK, vol. 15, No. 1, Dec. 15, 2018 (Dec. 15, 2018), pp. 151-155; DOI: 10.3923/ijp.2019.151.155; ISSN: 1811-7775, XP055753970.
Maged Mohamed Maher Abou-Hashem et al. "Induction of sub-GO arrest and apoptosis by seed extract of Moringa peregrina (Forssk.) Fiori in cervical and prostate cancer cell lines"; Journal of Integrative Medicine, vol. 17, No. 6, Nov. 1, 2019 (Nov. 1, 2019), pp. 410-422 DOI:10.1016/j.joim.2019.09.004; ISSN: 2095-4964, XP055754018.
S Majali Ibrahim et al. "Assessment of the antibacterial effects of Moringa peregrina extracts"; African Journal of Microbiology Research, vol. 9, No. 51, Dec. 28, 2015 (Dec. 28, 2015), pp. 2410-2414; DOI: 10.5897/AJMR2015.7787; XP055754048.
International Application No. PCT/EP2021/063690 Filed May 21, 2021; International Search Report; Authorized Officer: Jesko Bars dated Jul. 6, 2021; 7 pgs.
Indian Office Action dated Jan. 24, 2023.
D5-D7—AM05/2179 Ainthennai Thylam, Ak/2525 ¹u¾kam|lak¢dyamtailam, AK9/1120 Kasisadhya Ghrta.
Saudi Arabian Office Action dated May 7, 2023.
69880—PubChem CID: NCBI (2023). PubChem Compound CID 69980, Furan-2,5 dicarbaldehyde, (Mar. 26, 2005).

*Primary Examiner* — Qiuwen Mi
(74) *Attorney, Agent, or Firm* — Tarolli, Sundheim, Covell & Tummino L.L.P.

(57) ABSTRACT

The invention relates to an extract of *Moringa peregrina* seeds rich in the compound 2,5-diformylfuran, more specifically an extract of the cake of said seeds, and to a process for extracting the extract. The invention also relates to cosmetic or nutricosmetic compositions comprising said extract and to the use of said compositions for improving the appearance of the skin, mucous membranes or the integuments, for relaxing, soothing and destressing the skin and for preventing and/or combating the signs of aging and/or photoaging of the skin, and for preventing age spots.

9 Claims, No Drawings

MORINGA PEREGRINA SEED EXTRACT RICH IN 2,5-DIFORMYLFURAN, PROCESS FOR OBTAINING SAME AND USE THEREOF IN COSMETIC COMPOSITIONS

TECHNICAL FIELD

The invention relates to the cosmetic and nutricosmetic field and more particularly to the field of active ingredients included in the formulation of skincare compositions. The invention relates to an extract of *Moringa peregrina* seeds which is rich in the compound 2,5-diformylfuran (DFF). The invention also relates to the process for obtaining a particular extract of *Moringa peregrina* seeds, to cosmetic compositions comprising such extracts and, finally, to the cosmetic or nutricosmetic use of such compositions for caring for the skin, the scalp and the integuments.

TECHNICAL BACKGROUND

The Moringaceae are a mono-generic family (only one genus, *Moringa* adans), an element of the Saharo-Sindian flora, constituted of between 12 and 14 species according to the authors, distributed from Eastern Africa to Asia. The genus is conventionally divided into three sections which are, however, not confirmed as monophyletic by the phylogenetic analyses. Said analyses have rather revealed clades centered on certain morphological characters: pachycauls ("bottle trees"); "tuberous trees" and those that are neither bottle trees nor tuberous trees ("slender trees"). The species *Moringa peregrina* (Forssk.) Fiori, belongs to the third group. The sparse genetic studies on the genus or the family confirm the reality of the species relative to the other species in the genus, notably with respect to Indian *Moringa*, *Moringa oleifera* Lam. (see notably the articles: OLSON, M. E. 2002, Combining Data from DNA Sequences and Morphology for a Phylogeny of Moringaceae (Brassicales), *Systematic Botany* 27(1): 55-73; HASSANEIN, A. M. A. AND AL-SOQEE, A. A., 2018, Morphological and genetic diversity of *Moringa oleifera* and *Moringa peregrina* genotypes, Horticulture, Environment and Biotechnology 59(2): 251-261). A recent article on *Moringa peregrina* sampled on various locations in Saudi Arabia concluded, by using ITS markers, that there was genetic stability of the species (ALAKLABI, A., 2015, Genetic diversity of *Moringa peregrina* species in Saudi Arabia with ITS sequences, *Saudi Journal of Biological Sciences* 22: 186-190) with, however, a high level of intra-population genetic variation.

The species *Moringa peregrina* is found in the rocky environments of Yemen, Oman, Saudi Arabia, Eastern Africa, Sudan, Ethiopia, Eritrea, Somalia and Djibouti. Its presence in Iran appears limited to the south-eastern provinces, but this requires confirmation (PROTA14=MUNYANZIZA E. AND YONGABI K. A., Vegetable oils/Oleaginous plants, *Moringa peregrina* (Forssk.) Fiori, http://database.prota.org/protahtml/moringa peregrina_fr.htm, accessed on Oct. 23, 2019). In the Middle East and in Egypt, the species is now only represented by rare dispersed relicit stations (with the exception of a few populations at altitude), mainly in the sectors of the Sudan area. *Moringa peregrina* is today also considered as being rare and in danger in Sudan and Yemen. Relative to the other species of its clad, *Moringa peregrina* occupies the most arid and inhospitable habitats. It is apparently more drought-resistant than *Moringa oleifera* which is planted commercially on a large scale in the tropical and subtropical zones. Recent studies have shown that the size and girth of the seeds had a favorable impact on the germination time and the rate and speed of growth of the young individuals (GOMAA N. H. AND PICÓ F. X., 2011, Seed germination, seedling traits, and seed bank of the tree *Moringa peregrina* (Moringaceae) in a hyper-arid environment, *American Journal of Botany* 98(6): 1024-1030), indicating an adjustment in the allocation of resources regarding the seed quality rather than the number, which enables *Moringa peregrina* to reproduce efficiently in extreme (hyper-arid) abiotic environments. *Moringa peregrina* seeds have a thicker central mesotesta, in terms of cell layer, than those of *Moringa oleifera*.

A few historical reports exist which tend to indicate that *Moringa peregrina* oil was actively traded at the dawn of Islam in the region of Al-Ula (NASEEF, A. A. S., 1995, *Al-'Ulā, A study of Cultural and Social Heritage*). The oil produced locally from *Moringa peregrina* is nowadays mainly destined for personal consumption or for local markets.

In Saudi Arabia, the leaves were traditionally used as a decoction for internal use for treating diabetes, bowel diseases, ocular diseases and anemias (ABDEL-KADER, M. S., HAZAZI A. M. A., ELMAKKI O. A. AND ALQASOUMI S. I., 2018, A survey on the traditional plants used in Al Kobah village, *Saudi Pharmaceutical Journal* 26(6): 817-821) and as a diuretic, rubefacient and astringent (AQEEL A. A. M., TARIQ M., MOSSA J. S., AL-YAHYA M. A. AND AL-SAID M. S., 1984, "Plants used in Arabian Folk medicine", *Report submitted to Saudi Arabian National Centre for Science and Technology*, Riyadh, Saudi Arabia). In Oman, the oil, extracted by women at the end of the summer, is used to combat migraine, fever, burns, lacerations and fractures, constipation and stomach pains, and to combat muscular pain, dryness of the hair and labour pains (GHAZANFAR S. A., 1994, *Handbook of Arabian Medicinal Plants*, $1^{st}$ ed., CRC Press, Boca Raton, Ann Arbor, U.S.; GHAZANFAR S. A., 1998, Plants of Economic Importance, cap. 15, in GHAZANFAR, S. A. AND FISHER, M. (ed.) Vegetation of the Arabian Peninsula. Geobotany 25, pages 241-264, Kluwer Academic Publishers, table 11.1, page 247 and 11.7 page 251). It was also used in fragranced compositions (GHAZANFAR S. A., 1998, page 259) and in Oman and Yemen as a face lotion (GHAZANFAR S. A. AND RECHINGER B., 1996, Two multi-purpose seed oils from Oman. Plants for Food and Medicine. *Paper presented at the joint meeting of the Society for Economic Botany and International Society for Ethnopharmacology*, Jul. 1-7, 1996, London).

Extracts originating from *Moringa oleifera* seeds are known in the cosmetic field. For example, FR 296 879 discloses an extract of whole seeds (with teguments) of *Moringa oleifera* containing oil (including triglycerides, fatty acids and polar lipids) and polyphenols, and the use thereof in cosmetic compositions for combating aging of the skin. In said document, it is the apolar part of the *Moringa oleifera* seed which appears to be active, and more particularly the oily part. It is also known from FR 2 776 519 that protein extracts from *Moringa oleifera* seeds, which are known for their clarifying effects on turbid waters, have a softening, physiological conditioning, moisturizing, restructuring and repairing effect and have an effect as antipollution active agents on the skin and mucous membranes. In said document, the active principles are proteins with molecular weights of between 6500 and 8800 Da, which are obtained by aqueous extraction of *Moringa oleifera* cake. FR 3 076 460 is also known, which relates to the use of a protein extract of non-germinated and de-oiled *Moringa oleifera* seeds for treating sensitive, sensitized, reactive, fragile and/or embrittled skin and/or mucous membranes and/or in the treatment and/or prevention of erythema, in particular diaper rash of infants. In said document, the extraction process enables the production of a major fraction of proteins with molecular weights of about 8800 Da. KR2013/0088224 also discloses the use of an extract of germinated whole *Moringa oleifera* seeds in cosmetics, in particular obtained by extraction using a supercritical fluid. Said process makes it possible to isolate apolar amino acids and carotenoids, which are described as active agents for bleaching cosmetic use. All the abovementioned documents relate to the use of the species *Moringa oleifera*; none of them describes the use of the species *Moringa peregrina* in the cosmetic field. XP055753955, 2011, by Kolheil et al., discloses the extraction with ethanol, from the whole seeds of *Moringa peregrina*, of bioactive polyphenolic compounds, tannins, flavonoids, saponins, unsaturated sterols and/or triterpenes. The extract obtained is stored at 4° C. and has an antioxidant effect. XP055753970, 2018, by Abbas Alba et al., discloses an ethanolic extraction performed for three or more days on the whole seeds of *Moringa peregrina*. The filtrates are concentrated under reduced pressure at a temperature of between 45 and 50° C. XP055754018, 2019, from Abou-Hashem et al., discloses an ethanolic extraction performed for 3×72 hours on the whole seeds of *Moringa peregrina*. The extract obtained is then filtered and concentrated on a rotary evaporator at a temperature of about 45° C. XP055754048, 2015, from Majali Ibrahim et al., discloses an extraction with ethanol with stirring for 30 minutes, on the whole seeds of *Moringa peregrina*, followed by precipitation over 72 hours. None of the abovementioned documents discloses ethanolic extraction on the cake of unshelled *Moringa peregrina* seeds.

More specifically, for the species *Moringa peregrina*, it is known that certain phenolic and flavonoid compounds obtained from the leaves or whole seed of *Moringa peregrina* have antioxidant activity (AL-DABBAs M., 2017, Antioxidant activity of different extracts from the aerial part of *Moringa peregrina* (Forssk.) Fiori, from Jordan, *Pakistan Journal of Pharmaceutical Sciences*, 30(6): 2151-2157). These compounds are extracted with solvents such as methanol, ethyl acetate or hexane from the leaves or the whole seeds. It appears that it is the leaves which comprise the largest amount of active compounds.

Thus, depending on the species used in the genus *Moringa*, it is observed that, depending on the plant part (leaf or seed), the seed part (whole seed or otherwise, shelled or unshelled) and the extraction process performed, notably the choice of solvent, the molecules extracted prove to be different. Now, the composition of the extract conditions the biological activity and consequently the cosmetic efficacy.

Given the foregoing, one problem that the invention proposes to solve is that of developing novel products based on an extract of the species *M. peregrina* of the genus *Moringa* that may be used in cosmetics and that are easy to use.

Accordingly, the Applicant has revealed a novel extract obtained from the seeds and more specifically from the cake of the seeds of the species *Moringa peregrina*, which notably shows relaxing and antistress activity on the skin, antiaging activity and also preventive activity toward age spots. The extract according to the invention is rich in 2,5-diformylfuran (DFF), also known as 2,5-furandicarboxaldehyde. The extract is specifically obtained from the seeds or, more specifically, from the cake of the unshelled seeds of *Moringa peregrina*, notably via alcoholic extraction. The extract according to the invention is novel in two respects in the cosmetic field relative to the extracts of the prior art, firstly owing to the specific species of origin used and secondly owing to its particular compound content.

By the intergovernmental agreement of Apr. 10, 2018 between the government of the French Republic and the Kingdom of Saudi Arabia, the Applicant, Agence Française Pour Le Développement d'AlUla (AFALULA) and the Commission Royale pour AlUIA (RCU) notably have the joint project of developing sustainable agriculture and the local economy, notably for the local production of natural products derived from indigenous plants and of protecting the biodiversity and the rights of the AlUla region of the Kingdom of Saudi Arabia. The Kingdom of Saudi Arabia is a member of the Nagoya Protocol since Oct. 8, 2020. At the time of drafting of the present patent, the implementing regulations in respect of which the Nagoya Protocol will be integrated into the relevant aspects of local law is under examination. Consequently, at this stage, the Kingdom of Saudi Arabia has no specific requirements as regards the present patent application and the Nagoya Protocol. Thus, at the date of filing of the patent application, there are no certificate of compliance requirements regarding access to genetic resources.

SUMMARY

A first subject of the invention is an extract of *Moringa peregrina* seeds which is rich in the compound 2,5-diformylfuran. The compound 2,5-diformylfuran is a compound of saccharide nature that is rare in the plant kingdom and that is synthesized from furfural via the intermediate synthesis of 5-hydroxymethylfurfural.

By virtue of its particular feature of having a high concentration of 2,5-diformylfuran, the extract according to the invention is unique in the genus *Moringa*. It will be demonstrated that the species *Moringa peregrina* has a particular molecular profile different from those known from the other species of the genus, notably from the species *Moringa oleifera*, which the Applicant has managed to reveal.

A second subject of the invention is a process for obtaining an extract of *Moringa peregrina* seeds according to the invention, comprising the following steps in which:

a) the unshelled seeds of *Moringa peregrina* are collected and dried to obtain an internal moisture content of less than 8%, b) the dried seeds are pressed so as to separate the oil from the rest of the seed, to obtain the cake, c) the cake obtained in step b) is milled, d) the milled material obtained in step c) is dispersed, in a proportion of about 25% by weight of solid material relative to the total weight used, in a predominantly alcoholic solvent, the alcohol being chosen from ethanol or methanol optionally with a cosolvent such as a polyol or subcritical water, in a proportion of from 80% to 100% by weight of alcohol relative to the total weight of the solvent;

e) a solid-liquid extraction is performed, with stirring, at a temperature of between 16 and 30° C. over a period of about 2 hours, f) the liquid and solid phases are separated so as to remove the solid phase and to recover a liquid *Moringa peregrina* cake extract, and g) optionally, the liquid *Moringa peregrina* extract obtained is dried so as to obtain a solid *Moringa peregrina* extract.

A third subject of the invention is a cosmetic or nutricosmetic composition comprising, as active agent, an effective amount of an extract of *Moringa peregrina* seeds according to the invention and a physiologically acceptable excipient.

Lastly, a fourth subject of the invention is the cosmetic or nutricosmetic use of a composition according to the invention, for improving the appearance of the skin, mucous membranes or the integuments, for relaxing, soothing and destressing the skin and for preventing and/or combating the signs of aging and/or photoaging of the skin, and for preventing age spots.

BRIEF DESCRIPTION OF THE FIGURES

The invention will be better understood and further aims, details, features and advantages thereof will appear more clearly from the following description of several particular embodiments of the invention, given merely for illustration and without limitation.

DESCRIPTION OF THE EMBODIMENTS

In this description, unless otherwise specified, it is understood that when a range is given, it includes the upper and lower limits of said range.

In the present invention, the following abbreviations have the meanings given below:

MTT: 3-(4,5-dimethylthiazol-2-yl)-2,5-diphenyltetrazolium bromide (the MTT test is a rapid method for counting live cells)
SDS: Sodium Dodecyl Sulfate
PBS: Phosphate-Buffered Saline
ELISA: Enzyme-Linked Immunosorbent Assay
PCR: Polymerase Chain Reaction
ANOVA: Analysis Of Variance
MSH: Melanocyte Stimulating Hormone In the present invention, the following definitions apply:

"extract rich in the compound 2,5-diformylfuran": an extract containing an amount of the compound 2,5-diformylfuran greater than that of the other identified ingredients, i.e. an amount of greater than 50% relative to the dry matter of the total extract.

"effective amount": the necessary amount of active molecules to obtain the desired result, namely making it possible notably to obtain protection of the extracellular matrix of the skin.

"topical application": applying or spreading the active principle according to the invention, or a composition containing same, onto the surface of the skin, a mucous membrane or the integuments.

"physiologically acceptable": suitable for topical use, in contact with human skin, or for use via other routes of administration, for example orally or by injection into the skin, without any risk of toxicity, incompatibility, instability or allergic response.

"cake": the de-oiled part of the seed after pressing. It is the solid residue from the extraction of the oil from the seeds. It is a co-product of the grinding operation, the process for manufacturing the oil. It generally represents from 50% to 75% of the mass of the seeds.

"unshelled seeds": means that the shell, or pericarp, of the harvested seeds is kept around the seeds.

"when the fruit is ripe": means that the fruit is ripe, preferentially when the pod is at the start of dehiscence and turns a dark beige to brown color and when a 180° twist of the lower quarter of the pod brings about opening of the valves.

"predominantly alcoholic solvent": means that the solvent of alcoholic type may comprise a cosolvent having the sufficient characteristics for extracting the active principle, given that 96° pure ethanol appears to be the most suitable alcoholic solvent.

"about": a margin of plus or minus 10% to 20% relative to the given information (duration, percentage, etc.).

"active molecule", also referred to as the "active principle": the 2,5-diformylfuran molecule extracted according to the process of the invention from the *Moringa peregrina* seeds. This molecule is responsible for the biological activities described in the present invention.

"active agent": a sufficient amount of an extract according to the invention to obtain the biological activities described. Depending on whether the extract is liquid or dried, and concentrated or otherwise, the amounts of the active agent may vary in proportions of from 0.002% to 20% by weight relative to the total weight of the composition.

"signs of aging of the skin": any modification in the outer appearance of the skin and the integuments due to aging, for instance wrinkles and fine lines, wizened skin, sagging skin, thinning skin, lack of elasticity and/or tone of the skin, dull, lackluster skin or pigmentation spots on the skin, hair discoloring or nail stains, but also any internal modification of the skin that is not systematically reflected by a modified outer appearance, for instance any internal degradation of the skin following exposure to ultraviolet (UV) radiation.

A first subject of the invention relates to an extract of *Moringa peregrina* seeds which is rich in the compound 2,5-diformylfuran. The 2,5-diformylfuran molecule, also known as 2,5-furandicarboxaldehyde, has never been characterized in an extract of seeds of species of the genus *Moringa*. The species *Moringa peregrina* grows in very arid climates. Thus, its ability to withstand drought has enabled it to acquire unique features, which the Applicant has been able to identify via the use of an extraction process adapted to the whole seeds or, preferentially, to the seed cake.

In the context of the present invention, the plant part chosen is the *Moringa peregrina* seed. It is known that *Moringa peregrina* seeds are used for extraction of the oil known as *peregrina* oil (INCI name: *Moringa peregrina* seed oil), which is used regionally for personal consumption or in various traditional medicinal indications. The cake obtained after the seed has been de-oiled is a waste product that is currently notably used for animal feed.

According to the first object of the invention, the *Moringa peregrina* extract is obtained by solid-liquid extraction of the unshelled seed cake, with stirring, in a proportion of about 25% by weight of solid matter relative to the total weight used in a predominantly alcoholic solvent, the alcohol being chosen from ethanol or methanol optionally with a cosolvent such as a polyol or subcritical water, in a proportion of from 70% to 100% by weight of alcohol relative to the total weight of the solvent, at a temperature of between 16 and 30° C. for a period of about 2 hours, and by separation of the liquid and solid phases so as to remove the solid phase and to recover a liquid extract of *Moringa peregrina* seed, said extract being rich in the compound 2,5-diformylfuran. Preferably, the extract according to the invention is obtained from the cake of the seeds harvested, when the *Moringa peregrina* fruit is ripe, after extraction of the *peregrina* oil (INCI name: *Moringa peregrina* seed oil).

It should be pointed out that the active principle of the extract according to the invention, namely 2,5-diformylfuran, is a molecule of mixed polarity which has a certain fragility. Thus, the extract obtained from the whole unshelled seed should undergo selective extraction to obtain a high concentration of active principles, using suitable solvents and cosolvents and a temperature not exceeding 30° C.

The cosolvents may be, for example, glycol ethers (monopropylene or dipropylene glycol, propanediol, and other propylene glycol derivatives, ethylene or diethylene glycol derivatives) glycerol, dimethyl ether isosorbide, methyl or ethyl or propyl esters of fatty acids; dicaprylyl carbonate, dicaprylyl ether, alkyl acetate or propionate, acetone, methyl or ethyl ketone, and monoterpenes such as α-pinene or limonene. These cosolvents may be mixed with the primary solvent (e.g. ethanol or methanol) in proportions of from 0 to 30% (V/V).

The extraction conditions may be under atmospheric pressure or under vacuum or under an inert atmosphere, but preferentially in the dark at a temperature of between 16 and 30° C.

In a preferential embodiment according to the invention, the extract is obtained from the unshelled seed cake by solid-liquid extraction, with an alcoholic solvent, 96° ethanol.

In yet another embodiment, the liquid extract obtained is dried so as to obtain a dry extract of the *Moringa peregrina* seed cake containing more than 50% by weight of 2,5-diformylfuran relative to the total weight of the dry matter.

The dry extract of the *Moringa peregrina* seed cake more precisely contains about 55% by weight of 2,5-diformylfuran, 2.5% furfural, 1.2% isopropyl myristate, 4.7% palmitic acid, 11.1% oleic acid and 25.8% triglycerides relative to the total weight of the dry matter.

A second subject of the invention is a process for obtaining an extract of *Moringa peregrina* seed cake according to the invention, comprising the following steps in which:

a) the unshelled seeds of *Moringa peregrina* are collected and dried to obtain an internal moisture content of less than 8%, b) the dried seeds are pressed so as to separate the oil from the rest of the seed, to obtain the cake, c) the cake obtained in step b) is milled, d) the milled material obtained in step c) is dispersed, in a proportion of about 25% by weight of solid material relative to the total weight used, in a predominantly alcoholic solvent, the alcohol being chosen from ethanol or methanol optionally with a cosolvent such as a polyol or subcritical water, in a proportion of from 70% to 100% by weight of alcohol relative to the total weight of the solvent;

e) a solid-liquid extraction is performed, with stirring, at a temperature of between 16 and 30° C. over a period of about 2 hours, f) the liquid and solid phases are separated so as to remove the solid phase and to recover a liquid *Moringa peregrina* cake extract, and g) optionally, when the alcohol is ethanol, the liquid *Moringa peregrina* extract obtained is dried so as to obtain a solid *Moringa peregrina* extract.

In a preferential embodiment, the unshelled seeds are collected, i.e. the shell of which seeds is kept, when the fruit is ripe and preferentially when the pod is at the start of dehiscence.

In a preferential embodiment, the seeds are dried to obtain an internal moisture content of about 6%, the drying preferentially being performed on a ventilated rack sheltered from sunlight, preferably under shade in the open air.

The dried seeds are then milled extemporaneously with being cold pressed, which allows the *peregrina* oil (INCI name: *Moringa peregrina* seed oil) to be mechanically separated from the rest of the compressed seed, i.e. the cake.

The cake is then mechanically milled with any type of mechanical mill such as a hammer mill, flail mill, knife mill or crushing/shredding mill.

The extraction is advantageously always performed with stirring, thus allowing dispersion and homogenization of the solid in the liquid, improving the diffusion of the solute in the solvent.

To predominantly extract the compound of interest, 2,5-diformylfuran, an alcoholic solvent such as 96° ethanol will be preferred, but methanol may also be used, with a cosolvent such as a polyol or subcritical water. At the end of the extraction, the residual plant material, depleted of the compound of interest, is advantageously separated from the liquid phase by clarifying filtration. Even more preferably, the solvent is 96° ethanol. A liquid extract comprising between 0.5% and 1.6% of dry matter will advantageously be obtained from the *Moringa peregrina* seed cake, this dry matter being composed of at least 50% 2,5-diformylfuran, which corresponds approximately to between 0.25% and 0.8% by weight of the total weight of the liquid extract.

In one embodiment of the production process according to the invention, the liquid *Moringa peregrina* extract obtained is purified by distillation, microfiltration, ultrafiltration and/or nanofiltration to concentrate the compound of interest of the extract, 2,5-diformylfuran, relative to the organic materials also extracted, notably relative to the remainder of the extracted material, such as the fatty substances and derivatives also extracted. These purification steps make it possible to concentrate the compound of interest at the expense of other extracted compounds as mentioned and also the solvent.

In another embodiment of the production process according to the invention, the liquid extract obtained is dried so as to obtain a dry extract of the *Moringa peregrina* seed cake containing more than 50% by weight of the compound of interest, 2,5-diformylfuran, relative to the total weight of the extracted dry matter.

According to an advantageous embodiment of the invention, when the solvent is ethanol, the liquid *Moringa peregrina* seed extract obtained is preferentially dried, for example, by atomization, lyophilization or zeodration so as to obtain a solid *Moringa peregrina* seed cake extract, the ethanol having been evaporated off. The drying may be performed in the presence of an organic support such as maltodextrin, cyclodextrin or inulin, or in the presence of a mineral support such as phyllosilicate, magnesium silicate or carbonate and salts thereof.

The invention also relates to the extract of the *Moringa peregrina* seeds which may be obtained via the production process according to the invention.

A third subject of the invention is a cosmetic or nutricosmetic composition comprising, as active agent, an effective amount of an extract of *Moringa peregrina* seeds according to the invention and a physiologically acceptable excipient.

The composition according to the invention may be formulated in the form of various preparations suitable for topical administration or for oral administration.

According to a first variant, the various preparations are suitable for topical administration and include creams, oil-in-water and water-in-oil emulsions, milks, ointments, lotions, oils, balms, aqueous or aqueous-alcoholic or glycolic solutions, sera, powders, patches, sprays or any other product for external application, for instance medical devices or cosmetic-textile products.

According to a second variant, the various preparations are suitable for oral administration; the plant extract comprising the active compound 2,5-diformylfuran which may be included either in a food composition or in a food supplement. The food supplement may be in the form of hard gel capsules or soft gelatin or vegetable capsules in the context of the present invention. Said food supplement may then contain from 0.01% to 100% by weight of the plant extract. More preferentially, the amount of plant extract is from 0.02% to 40% by weight and in particular from 0.2% to 20% by weight relative to the total weight of the composition.

In the context of a food use, for nutritive or cosmetic (cosmeto-food or nutricosmetic) purposes, the composition will advantageously be formulated in the form of a preparation that is suitable for oral administration. It may comprise no excipient and may be constituted, in its entirety, of the plant extract comprising the active compound 2,5-diformylfuran.

According to a preferential embodiment, the compositions according to the invention are more particularly intended for topical administration. These compositions must thus contain a cosmetically acceptable medium, i.e. a medium that is compatible with the skin and the integuments, and cover all cosmetic forms. These compositions may notably be in the form of creams, oil-in-water or water-in-oil emulsions or multiple emulsions, sera, solutions, suspensions, gels, milks, lotions, sticks or even powders, and may be suitable for application to the skin, the lips and/or the integuments. These compositions comprise the excipients that are necessary for their formulation, such as solvents, emollients, thickeners, diluents, surfactants, antioxidants, bioactive agents, dyes, preserving agents and fragrances. They may be used as a skincare products and/or as skin makeup products.

The composition according to the invention may in particular consist of a haircare composition, and notably a shampoo, a hair conditioner, a treating lotion, a styling cream or gel, a hair restructuring lotion, a mask, etc. The cosmetic composition according to the invention may notably be used in treatments involving an application which may or may not be followed by rinsing, or alternatively in the form of a shampoo. The composition according to the invention may advantageously be used in antidandruff treatments. It may also be in the form of a dye or mascara to be applied with a brush or a comb, in particular to the eyelashes, the eyebrows or the hair.

The compositions according to the invention also comprise any additive commonly used in the envisioned field of application and also the adjuvants required for their formulation, such as solvents, thickeners, diluents, antioxidants, dyes, sunscreens, self-tanning agents, pigments, fillers, preserving agents, fragrances, odor absorbers, cosmetic or pharmaceutical active agents, essential oils, vitamins, essential fatty acids, surfactants, film-forming polymers, etc.

The INCI Dictionary & Handbook ("International Nomenclature of Cosmetic Ingredients" (13th edition, 2010) published by The Personal Care Products Council Inc., Washington, D.C.) describes a wide variety, without limitation, of cosmetic and pharmaceutical ingredients commonly used in the skincare industry, which are suitable for use as additional ingredients in the compositions according to the present invention.

In any case, a person skilled in the art will take care to ensure that these adjuvants and the proportions thereof are chosen such that the desired advantageous properties of the composition according to the invention are not adversely affected.

According to one advantageous embodiment of the invention, the amount of plant extract in the composition according to the invention is from 0.002% to 20% by weight, and in particular from 0.001% to 10% by weight relative to the total weight of the composition.

Lastly, a fourth subject of the invention is the cosmetic or nutricosmetic use of a composition according to the invention, for improving the appearance of the skin, mucous membranes and the integuments, for relaxing, soothing and destressing the skin and for preventing and/or combating the signs of aging and/or photoaging of the skin, and for preventing age spots.

According to one embodiment the aim of the use according to the invention is more particularly to relax, soothe and destress the skin and to combat the signs of aging of the skin.

According to another embodiment, the aim of the use according to the invention is to prevent the appearance of age spots.

Although the invention has been described in relation with several particular embodiments, it is quite obvious that it is not in any way limited thereto and that it encompasses all the technical equivalents of the means described and also combinations thereof if they fall within the context of the invention.

The use of the verb "contain", "comprise" or "include" and its conjugated forms does not exclude the presence of elements or steps other than those stated in a claim.

In the claims, any reference sign in parentheses shall not be interpreted as a limitation of the claim.

EXAMPLES

Example 1: Preparation of a Plant Extract from *Moringa* Peregrine Cake

Unshelled seeds of *Moringa peregrina* (Forssk.) Fiori harvested when the fruit is ripe were dried to obtain an internal moisture content of less than 8% and preferentially about 6%, and then pressed with a mechanical endless screw press, so as to separate the oil from the rest of the seed in order to obtain, on the one hand, the virgin oil and, on the other hand, a cake. The cake is then isolated in the form of precut rolls in pieces of 1 to 2 cm. On the cake preheated for 10 minutes at 55° C., a maceration and extraction are performed with 96° ethanol preheated for 10 minutes at 55° C. in a ratio of 25%/75% (m/m), the mixture is sheared with a blender for 15 minutes and is then left to stir with by impeller for 2 hours at a temperature of between 16° C. and 30° C. The product is then filtered through a Büchner funnel under vacuum to obtain a pale yellow filtrate containing 1.15% dry matter. The liquid extract obtained is referred to hereinbelow as the "*peregrina* extract according to the invention" or the "peregrine extract" or the "peregrine cake extract". This liquid extract is subsequently used in the various efficiency tests.

This *peregrina* extract according to the invention contains 1.15% dry matter, itself including (results expressed relative to dry matter (DM):

TABLE 1

| | Total compounds in DM | | % |
|---|---|---|---|
| Active compounds | Furfural | 2.528 | 57.18 |
| | 2,5-Furandicarboxaldehyde | 54.66 | |
| Fatty substance of plant origin | Isopropyl myristate | 1.175 | 42.812 |
| | Palmitic acid | 4.713 | |
| | Oleic acid | 11.093 | |
| | Triglycerides | 25.831 | |

The dry extract described above is obtained via a gravimetric method based on the mass before and after evaporation present in the liquid extract.

2,5-Furandicarboxaldehyde or 2,5-diformylfuran is the active principle of this extract. It was assayed by a chromatographic method, and more precisely by gas chromatography coupled to a flame ionization detector.

The furfural was assayed by an identical method.

The isopropyl myristate was assayed by an identical method.

The palmitic and oleic acid were assayed by an identical method.

The triglycerides were isolated by ultracentrifugation.

Example 2: Effect of the *Peregrina* Extract According to the Invention as an Antioxidant The object of this study is to evaluate the modulation of the antioxidant activity by the *peregrina* extract in an acellular in vitro colorimetric model using the DPPH (2,2-diphenyl-1-picrylhydrazyl) radical and also the reference antioxidant, ascorbic acid. The method used is known as inhibition. It is based on the degradation of the violet-colored oxidizing radical DPPH, which absorbs at 540 nm, with a reference antioxidant, ascorbic acid. This reaction serves as a positive control and leads to the formation of the DPPH compound which is colorless or even pale yellow. The *peregrina* extract according to the invention and the reference product "ascorbic acid" are placed in contact with the DPPH solution for 30 minutes at 40° C. The antioxidant activity is then evaluated by measuring the absorbance at 540 nm. The modulation of this activity is expressed as a percentage of stimulation of the antioxidant activity by the test active agent, with, for reference, the maximum antioxidant activity obtained in the presence of ascorbic acid ($T_+$).

Protocol: A DPPH solution is incubated for 30 minutes at 40° C., in the absence (control) or in the presence of the *peregrina* extract according to the invention ($T_+$) and at decreasing concentrations of the test sample. At the end of the incubation period, the antioxidant activity in the presence of the reference product and in the presence or absence of the *peregrina* extract was revealed by staining after 30 minutes at 40° C. It was thus evaluated by measuring the absorbance of the reaction medium at 540 nm. For each concentration tested, the modulation of the antioxidant activity with the test product is calculated according to the following formula.

Percentage modulation of antioxidant activity=100× [($OD_{540}$ Control−$OD_{540}$ Test product)/$OD_{540}$ Reference product]. [Math. 1]

If the result is negative, the test product will be considered as oxidizing; if the result is positive, the percentage will be expressed as stimulation of the free-radical-scavenging activity. The results obtained are given below.

TABLE 2

| | | DPPH Inhibition |
|---|---|---|
| *Peregrina* extract according to the invention | 2% | 36 |
| | 1.0% | 23 |
| | 0.1% | 5 |

Conclusion: the *peregrina* extract according to the invention is capable of protecting against free radicals: it has significant antioxidant properties at and above a concentration of 1%.

Example 3: Effect of the *Peregrina* Extract According to the Invention as a Metalloprotease Inhibitor The object of this study is to evaluate the modulation of the metalloprotease-inhibiting activity by the *peregrina* extract according to the invention in an in vitro acellular model using a type I collagenase and a hyaluronidase, a substrate complex and a chromophore, ninhydrin. A buffered solution of type I collagenase and hyaluronidase reacts with a specific substrate complex and transforms it to form a compound that is capable of activating a chromophore by incubation at 80° C. for 15 minutes. The collagenase and hyaluronidase activities may thus be evaluated by measuring the absorbance at 565 nm. The sample is placed in contact with the collagenase and hyaluronidase solution together with the enzyme substrate complex at 37° C. for 5 minutes. The substrate transformed with the enzymes is capable of activating the chromophore by incubation at 80° C. for 15 minutes. The collagenase and hyaluronidase activities in the presence/absence of the sample are then evaluated by measuring the absorbance at 565 nm. The modulation of this activity is expressed as a percentage of inhibition or of activation of the collagenase and hyaluronidase activity in the absence of the active agent, i.e. only in the presence of the enzyme substrate.

Protocol: A solution of type I collagenase and hyaluronidase enzymes is incubated in its substrate for 5 minutes, in the absence or presence of the tested *peregrina* extract according to the invention. The solutions are then placed in contact with the chromogen ninhydrin, followed by incubating for 15 minutes at 80° C. At the end of the incubation period, the activity of the collagenase and hyaluronidase enzymes with and without the test or reference product was evaluated by measuring the absorbance of the reaction media at 565 nm. For each concentration tested, the modulation of the collagenase and hyaluronidase enzymatic activities with the test product is calculated according to the following formula.

Percentage modulation of collagenase/hyaluronidase enzymatic activity=100×[(OD test or reference product−OD collagenase/hyaluronidase alone)/ OD collagenase/hyaluronidase alone]. [Math. 2]

If the result is negative, the percentage is expressed as enzyme inhibition; if the result is positive, the percentage is expressed as enzyme activation. The results of the metalloprotease inhibition with the *peregrina* extract according to the invention are given below.

TABLE 3

| | | Inhibition versus control (%) |
|---|---|---|
| Peregrina extract according to the invention | 1% | 87 |
| | 0.5% | 87 |
| | 0.1% | 88 |
| | 0.01% | 62 |

Conclusion: The *peregrina* extract according to the invention gives rise to strong metalloprotease (collagenase/hyaluronidase) inhibition of 62% at very low levels of 0.01%. The *peregrina* extract according to the invention is capable of strongly inhibiting these metalloproteases and has good potential for protecting the extracellular matrix of the skin with great efficiency and, via this inhibition, it reveals an antiaging effect.

Example 4: Effect of the *Peregrina* Extract According to the Invention on Inhibiting the Enzymes Histone Deacetylase (HDAC) and Sirtuin I The object of this study is to demonstrate the inhibitory activity of the *peregrina* extract according to the invention on the enzymes HDACs and sirtuin I. A buffered solution of HDACs & sirtuin I reacts with a substrate for 20 minutes at 37° C. and transforms it to form a compound which becomes stained in the presence of a developer after incubation at 37° C. for 10 minutes. The maximum deacetylating activity of the sirtuins may thus be evaluated by measuring the absorbance at 405 nm. The *peregrina* extract according to the invention or the reference product "trichostatin A (STA) inhibitor 1 µM" are placed in contact with the solution of sirtuins together with the enzyme substrate for 20 minutes at 37° C., and the substrate transformed with the enzyme is stained by adding a developer. The deacetylating activity of the HDACs and sirtuin I in the presence of the active agent is then evaluated by measuring the absorbance at 405 nm. The modulation of this activity is expressed as a percentage of inhibition or activation of the maximum activity of the HDACs and of sirtuin I in the absence of the active agent, i.e. only in the presence of the substrate for the HDAC and sirtuin I enzymes.

Protocol: A solution of sirtuin enzymes is incubated in its substrate for 20 minutes in the absence (control) or presence of the reference product, or of increasing concentrations of the test products. The *peregrina* extract according to the invention is tested at the following concentrations: 2%; 1%; 0.1% (V/V). At the end of the incubation period, the activity of the sirtuin enzymes with and without the test or reference product was revealed by staining using a developer solution (10 minutes at 37° C.) and evaluated by measuring the absorbance of the reaction media at 405 nm. For each concentration tested, the modulation of the deacetylating activity of the histone deacetylase and sirtuin I enzymes with the test product is calculated according to the following formula.

Percentage modulation of sirtuin enzymatic activity=100×[($OD_{405}$ test or reference product)−($OD_{405}$ HDACs and sirtuin I alone)]/$OD_{405}$ sirtuins alone. [Math. 3]

If the result is negative, the percentage is expressed as inhibition of the enzymatic reaction; if the result is positive, the percentage is expressed as activation of the enzymatic reaction. The results for the inhibition of the histone deacetylase (HDAC) enzymes are given below.

TABLE 4

| | Percentage | Inhibition versus control (%) |
|---|---|---|
| Peregrina extract according to the invention | 2% | 20 |
| | 1% | ns |
| | 0.10% | −18 |

Conclusion: At 2%, the *peregrina* extract according to the invention shows significant HDAC inhibition; this inhibition reflects the capacity for promoting the self-protection of skin cells against genetic drift, notably associated with the aging process. Thus the extract appears to be useful against one of the most common genetic drifts on the surface of the skin, namely fibrosis, which is manifested by the appearance of "skin tags" (fibrotic protuberances). The extract may advantageously interfere with fibrosis on the surface of the skin and thus prevent skin aging.

Example 5: Effect of the *Peregrina* Extract According to the Invention for Modulating the Antiinflammatory Activity of the Phospholipase-A2 Enzyme The object of this study is to evaluate the modulation of the antiinflammatory activity of the enzyme phospholipase A2 by one or more samples in an in vitro acellular model by means of the "SPLA2 (type V) Inhibitor Screening Assay Kit". Phospholipase A2 is a key enzyme upstream of the inflammatory process which is triggered by the arachidonic cascade. A buffered solution of phospholipase A2 reacts with a specific substrate, diheptanoyl thio-PC, and transforms it into a compound which binds to a chromogen, DTNB, with agitation at room temperature. The phospholipase A2 activity may thus be evaluated by measuring the absorbance at 413 nm. The *peregrina* extract according to the invention or the reference inhibitory product "thioetheramide-PC" are placed in contact with the phospholipase A2 solution at the same time as the enzyme substrate. The substrate transformed by the enzyme is stained by means of the chromogen DTNB by agitation at room temperature. The activity of the *peregrina* extract according to the invention or of the reference product is then evaluated by measuring the absorbance at 413 nm. The modulation of this activity is expressed as a percentage of inhibition or of activation of the phospholipase A2 activity in the absence of the active agent, i.e. only in the presence of the enzyme substrate (diheptanoyl thio-PC).

Protocol: A solution of the enzyme phospholipase A2 is incubated in its substrate, diheptanoyl thio-PC, in the absence or presence of the reference inhibitor and of the *peregrina* extract according to the invention, tested under the following conditions: 2%; 1%; 0.1% (V/V), and the chromogen DTNB is then incorporated, followed by incubation for 15 minutes at 25° C. At the end of the incubation period, the activity of the enzyme phospholipase A2 with and without the test product or the reference product is evaluated by measuring the absorbance of the reaction media at 413 nm. For each concentration tested, the modulation of the phospholipase A2 enzymatic activity with the test product is calculated according to the following formula.

Percentage modulation of phospholipase A2 enzymatic activity=100×[($OD_{405}$ test product or reference product−$OD_{405}$ sPLA2 alone)/$OD_{405}$ sPLA2 alone]. [Math. 4]

If the result is negative, the percentage is expressed as enzyme inhibition; if the result is positive, the percentage is expressed as enzyme activation. The results for the modulation of the antiinflammatory activity of the enzyme phospholipase-A2 are given below.

TABLE 5

| | | Inhibition versus Control (%) |
|---|---|---|
| Peregrina extract according to the invention | 2% | 19 |
| | 1% | 16 |
| | 0.10% | 11 |

Conclusion: The *peregrina* extract according to the invention generates a slight, stable inhibition of PLA2 at and above a dose of 0.1% but more preferably at 1% or 2%. This means that the *peregrina* extract according to the invention has the capacity for bringing about very early reduction of the arachidonic cascade/inflammation cascade; this extract thus has good soothing or relaxing potential on the skin.

Example 6: Effect of the *Peregrina* Extract According to the Invention on Inhibiting the Action of Endothelin-1

Endothelin is the most potent vasoconstrictor known in the human body. Moreover, endothelin depletion is also known to create a vasodilatory effect [Hirata, Y. et al., 1988, Cellular mechanism of action by a novel vasoconstrictor endothelin in cultured rat vascular smooth muscle cells, *Biochemical and Biophysical Research Communications*, 154: 3, pages 868-875] [Shalinkumar P. et al., 2018, H2S Mediates the Vasodilator Effect of Endothelin-1 in the Cerebral Circulation. *American Journal of Physiology. Heart Circulatory Physiology*, 315, pages 1759-1764].

The object is to assay the type-1 endothelin in human microvascular endothelial cells after exposure for 24 hours to the *peregrina* extract according to the invention.

Protocol: Human microvascular endothelial cells were supplied by the company PELOBiotech and cultured in 96-well plates according to the supplier's production procedures. The extracts are left to act at various concentrations on the endothelial cells at 80% of confluence for 24 hours, and the endothelin-1 in the cell supernatants is then quantified using the PicoKine ELISA kit (EDN1). A viability test is performed beforehand to define the nontoxic doses to be used in the endothelin-1 assay. The negative control is performed using cells in culture medium without treatment. The positive control in the viability test is 0.5% SDS. All the conditions are prepared in culture media, and the cells are subsequently incubated at 36.5° C./5% $CO_2$ for 24 hours.

a) Application of the Test Solutions to the Endothelial Cells:

The test products are placed in contact with endothelial cells at subconfluence in 96-well plates. For each concentration, the test is performed on three wells. The plates are incubated for 24 hours±1 hour at 36.5° C./5% $CO_2$.

b) Viability Test:

The cell viability is evaluated with the MTT method on the cells after incubation with the products. After incubation for 24 hours, the supernatants are recovered and stored at −20° C. for the assays. The wells are then rinsed once with 200 µL of PBS. 50 µL of a 0.5 mg/ml MTT solution are added to each well: incubation for 3 hours at 36.5° C./5% $CO_2$. 100 µL of isopropanol are added to each well. After homogenization, an absorbance reading at 550 nm is taken.

For each condition, the ratio of the mean optical density values of the cells to the mean optical density values of the negative controls determines the viability ratio.

c) Endothelin-1 Assay:

The assay is performed using the ELISA kit.

TABLE 6

| | Extract concentration | Cell growth versus control (%) | Endothelin 1 versus control (%) | Endothelin 1 versus control (pg/ml) |
|---|---|---|---|---|
| Peregrina extract according to the invention | 5% | −22.31 | −53.21 | −71.8 |
| | 1% | 0 | −11.61 | −15.66 |
| | 0.10% | −5.77 | −25.11 | −33.88 |

Conclusion: The viability test performed at the end of the treatment did not show any toxic effects for the concentrations tested. The endothelin-1 assay is performed in the cell supernatants at nontoxic concentrations. The amount of endothelin-1 for each condition is assayed using the ELISA kit. For the negative control cells, the values are of the order of 134.94 pg/ml. For the cells treated with various concentrations of extracts, the values are from 63.14 pg/ml (with 5% of the extract according to the invention) to 101.06 pg/ml (with 0.1% of the extract according to the invention), which shows very significant inhibitions at and above 0.1% of the extract according to the invention with about 25% inhibition of type-1 endothelin production and up to 53% inhibition with 5% of the extract according to the invention.

Example 7: Effect of the *Peregrina* Extract According to the Invention on Stimulating Telomerase Activity Telomeres are complexes which protect DNA, located at the end of linear chromosomes, promoting chromosome stability. Telomere shortness in humans is developing into a prognostic marker of the risk and progression of disease, and of premature mortality in many types of cancers, notably breast, prostate, colon, bladder, head and neck, lung, and kidney cells [Ornish D., 2008, Increased Telomerase Activity and Comprehensive Lifestyle Changes: a Pilot Study, *Lancet Oncology* 9, pages 1048-1057]. Telomere shortening is counteracted by the cellular enzyme telomerase.

The object of the study is to evaluate the effect of the compound known as "*peregrina* extract according to the invention" on telomerase activity in a model composed of adult human keratinocytes at a low passage level in monolayer culture.

Protocol: Human keratinocytes were obtained from a 49-year-old donor. To perform the experiments, the keratinocytes were used at a low passage level (i.e., cell isolation passage number 2). The cells were grown as a monolayer until they reached about 75% of confluence before being used in the experiment.

Reference product: FK228 at 100 ng/ml was used as a reference inducer of telomerase 1 activity.

Incubation protocol: The cells were incubated for 24 hours in the absence (control) or presence of the reference product or of increasing concentrations of test compounds such as the *peregrina* extract according to the invention at: 0.5; 1%; and 5% (v/v).

The *peregrina* extract according to the invention is diluted directly in the incubation medium to achieve the various concentrations described above.

Evaluation of the Effects:

—Protein Measurement

At the end of the incubation period, the total proteins of the cells were extracted from the cells and measured by means of a spectrocolorimetric method (Bradford method). This measurement is used to determine the exact volume of extract to use in the telomerase activity measurement, so as to maintain the same amount of protein (containing telomerase) for all the conditions tested in the PCR step.

—Measurement of the Telomerase Activity

At the end of the incubation period, the telomerase was extracted from the cells and its activity was determined by means of a specific, sensitive kit. The principle of the telomerase kit is to measure the telomerase activity by coupling a PCR step (in which telomerase functions as regards its elongation activity) with an ELISA step for semi-quantitative determination of amounts of telomerase elongation product.

—Statistics

The results are expressed in arbitrary units for the telomerase activity level (mean±S.D). The significance level between the "vehicle" and the "reference product" was evaluated by means of a Student's t test (*: $p<0.05$). The significance level between "control" and "test compound" was evaluated independently for each product by a one-way analysis of variance (one-way ANOVA) followed by a Holm-Sidak test (*: $p<0.05$).

The *peregrina* extract according to the invention, tested at 0.5% and 1% (v/v), did not significantly modulate the telomerase activity relative to the "control". When tested at 5% (v/v), the *peregrina* extract according to the invention significantly increased the telomerase activity by 18.9% ($p<0.001$), in comparison with the "control".

The reference product, named "FK228", tested at 100 ng/ml, significantly increased the telomerase activity by 28.0% ($p<0.01$). This result was expected and validates the experiment. The results for the stimulation of the telomerase activity are given below.

TABLE 7

|  | Concentration of the extract | Cell growth versus control (%) | Activity of telomerase versus control (%) |
| --- | --- | --- | --- |
| *Peregrina* extract according to the invention | 5.00% | +5.8 | +18.90 |
|  | 1.00% | ca. −2.2 | +4.00 |
|  | 0.50% | −2.6 | +2.30 |

Conclusion: the *peregrina* extract according to the invention, tested at 0.5% and 1% (v/v), did not significantly modulate the telomerase activity relative to the "control". When tested at 5% (v/v), the *peregrina* extract according to the invention significantly increased the telomerase activity by 18.9% ($p<0.001$) in comparison with the "control". The extract according to the invention acts directly on this enzymatic pathway which builds up protective telomere at the ends of chromosomes and slows down the natural aging of genetic material. The extract according to the invention can thus produce an antiaging effect on chromosomes.

Examples 2 to 7 demonstrate that the *peregrina* extract according to the invention has antiaging, antistress and relaxing properties which demonstrates the profile of a good skin protector.

Example 8: Effect of the *Peregrina* Extract According to the Invention on Stimulating Tyrosinase Activity The object of this study is to evaluate the activity on the enzyme tyrosinase of the *peregrina* extract according to the invention in an in vitro acellular model using a tyrosinase enzyme of fungal origin (Sigma-Aldrich ref. T3824), its substrate L-tyrosine (Sigma-Aldrich ref. T3754) and a reference inhibitor, hydroquinone (Sigma-Aldrich ref.H17902, inhibitor=hydroquinone 2.5 mM). A buffered solution of tyrosinase reacts with a substrate, L-tyrosine 2.5 mM, for 60 minutes at 23° C. and transforms it to form a colored compound. The maximum tyrosinase activity may thus be evaluated by measuring the absorbance at 475 nm. The *peregrina* extract according to the invention or the reference product "hydroquinone" are placed in contact with the tyrosinase solution together with the enzyme substrate for 60 minutes at 23° C.; the substrate transformed with the enzyme is naturally colored. The tyrosinase activity in the presence of the active agent is then evaluated by measuring the absorbance at 475 nm. The modulation of this activity is expressed as a percentage of inhibition or of activation of the maximum tyrosinase activity in the absence of the active agent, i.e. only in the presence of the enzyme substrate (L-tyrosine).

Protocol: A solution of tyrosinase enzyme is incubated in its substrate L-tyrosine for 60 minutes in the absence (control) or presence of the reference product, or of increasing concentrations of the *peregrina* extract according to the invention/concentrations; 2%; 1%; 0.1% (V/V). At the end of the incubation period, the activity of the tyrosinase enzyme with and without the test or reference product was evaluated by measuring the absorbance of the reaction media at 475 nm. For each concentration tested, the modulation of the tyrosinase enzymatic activity with the test product is calculated according to the following formula.

Percentage modulation of tyrosinase enzymatic activity=100×[(OD475 test product or reference product)−(OD475 tyrosinase alone)]/OD475 tyrosinase alone. [Math. 5]

If the result is negative, the percentage is expressed as enzyme inhibition; if the result is positive, the percentage is expressed as enzyme activation. The results for the stimulation of the tyrosinase activity are given below.

TABLE 8

|  |  | Activation versus Control (%) |
| --- | --- | --- |
| *Peregrina* extract according to the invention | 2% | 65 |
|  | 1% | 37 |
|  | 0.10% | 8 |

Conclusion: The *peregrina* extract according to the invention is capable of lowering the basal tyrosinase activity, which makes it possible to indicate that this extract has the capacity for increasing one of the natural forms of skin protection: protection against ultraviolet rays.

Example 9: Effect of the *Peregrina* Extract According to the Invention on Inhibiting Melanin Production The object of this study on human cell cultures is to collate all the data used, and also the results obtained, in order to perform the melanin modulation test on human melanocytes after exposure to the *peregrina* extract according to the invention for 5 days.

Protocol: Human melanocytes are cultured in 96- and 24-well plates.

The *peregrina* extract according to the invention is allowed to act on the confluent melanocytes at concentrations of 5%, 2%, 1% and 0.1% for 5 days. A pretest of viability with MTT after 24 hours makes it possible to evaluate the cytotoxicity and to choose the concentrations for the melanin modulation test. This modulation is evaluated by assaying the melanin in the cell lyzates after 5 days of exposure to the extracts. The negative control is performed using cells in culture medium without treatment. The positive control for the viability test is 0.5% SDS. For the melanin modulation test, media with and without α-MSH are used as negative controls.

All the conditions are prepared in culture media, and the cells are subsequently incubated at 36.5° C./5% $CO_2$ for 24 hours for the cytotoxicity test and 5 days for the melanin assay.

a) Application of the test solutions to the melanocytes: The test concentrations are placed in contact with the confluent melanocytes in 96-well plates (cytotoxicity test) and 24-well plates (melanin assay). For each concentration, the test is performed on three wells. The plates are incubated for 24 hours±1 hour and 5 days at 36.5° C./5% b) Viability test: The cell viability is evaluated with the MTT method on the cells after incubation for 24 hours with the products. After incubation for 24 hours, the intended wells are rinsed once with 200 μL of PBS. 50 μl of a 0.5 mg/ml MTT solution are added to each well and incubation is performed for 3 hours at 36.5° C./5% $CO_2$. 150 μL of isopropanol are added to each well. After homogenization, an absorbance reading at 550 nm is taken. For each condition, the ratio of the mean optical density values of the cells to the mean optical density values of the negative controls determines the viability ratio.

A viability cutoff value of 70% relative to the negative control value is used to classify the test substances as cytotoxic or noncytotoxic. A "noncytotoxic" classification is given on the in vitro results for a viability >70% and a "cytotoxic" classification is given for a viability ≤70%.

The 5% concentration of the extract according to the invention proved to be cytotoxic at 5% under the test conditions. The 2%, 1% and 0.1% concentrations are thus used for the melanin modulation test. The amount of melanin present in the cells is assayed after cell lysis. The results for the inhibition of melanin production are given below.

TABLE 9

| | Extract concentration | Cell growth versus control (%) | Melanin inhibition versus control (%) | Melanin content (μg/ml) |
|---|---|---|---|---|
| *Peregrina* extract according to the invention | 2% | −3.41 | +16.50 | 152 |
| | 1.0% | +13.46 | +65.90 | 62 |
| | 0.10% | +13.29 | +71.40 | 52 |

Conclusion: the *peregrina* extract according to the invention inhibits melanin production in cellulo, which gives it a skin-protecting property. This inhibition also shows a relaxing effect on melanocytes since the basal rate is lower than that of the control (absence of extract according to the invention in the culture medium); it is recalled that the production of melanin is a response to a cellular stress. Thus, the *peregrina* extract according to the invention demonstrates that it is capable of preventing age spots.

Example 10: Analytical Characterization of the Peregrine Extract According to the Invention Versus the *Oleifera* Extract with an Identical Extraction Process On the basis of *Moringa peregrina* cake and *Moringa oleifera* cake, the extraction process according to the invention described in example 1 was applied. The comparative composition of the ingredients extracted is given below on a dry matter basis.

TABLE 10

| Compounds | *Oleifera* (%) | *Peregrina* (%) |
|---|---|---|
| Acetic acid | 1.431 | — |
| 1-Hydroxy-2-propanone | 1.962 | — |
| Furfural | 6.140 | 2.528 |
| 2,5-Furandicarboxaldehyde (DFF) | 0.823 | 55.660 |
| Isopropyl myristate | 0.128 | 1.175 |
| Methyl palmitate | 0.230 | — |
| Palmitic acid | 10.356 | 4.713 |
| Ethyl palmitate | 0.399 | — |
| Methyl linoleate | 0.428 | — |
| Methyl oleate | 2.443 | — |
| Oleic acid | 47.844 | 11.093 |
| Ethyl oleate | 2.675 | — |
| Stearic acid | 5.064 | — |
| Bis(2-ethylhexyl) hexanedioate | 1.688 | — |
| Methyl 7-oxodehydroabietate | 0.327 | — |
| 2-Ethylhexyl 1,4-terephthalate | 0.655 | — |
| Total | 84.317 | 74.169 |

It is seen that the two extracts have a very different molecular profile. The extract of *Moringa oleifera* contains less than 1% of DFF, whereas the extract of *Moringa peregrina* contains more than 50% thereof.

Example 11: Comparative Test with *Moringa oleifera* for an in Tubo Collagenase Test The object of this study is to evaluate the modulation of the metalloprotease-inhibiting activity by the *peregrina* extract according to the invention in an in vitro acellular model using a type I collagenase and a hyaluronidase, a substrate complex and a chromophore, ninhydrin. A buffered solution of type I collagenase and hyaluronidase reacts with a specific substrate complex and transforms it to form a compound that is capable of activating a chromophore by incubation at 80° C. for 15 minutes. The collagenase and hyaluronidase activities may thus be evaluated by measuring the absorbance at 565 nm. The sample is placed in contact with the collagenase and hyaluronidase solution together with the enzyme substrate complex at 37° C. for 5 minutes. The substrate transformed with the enzymes is capable of activating the chromophore by incubation at 80° C. for 15 minutes. The collagenase and hyaluronidase activities in the presence/absence of the sample are then evaluated by measuring the absorbance at 565 nm. The modulation of this activity is expressed as a percentage of inhibition or of activation of the collagenase and hyaluronidase activity in the absence of the active agent, i.e. only in the presence of the enzyme substrate.

Protocol: A solution of type I collagenase and hyaluronidase enzymes is incubated in its substrate for 5 minutes, in the absence or presence of the tested *peregrina* extract according to the invention. The solutions are then placed in contact with the chromogen ninhydrin, followed by incubating for 15 minutes at 80° C. At the end of the incubation period, the activity of the collagenase and hyaluronidase enzymes with and without the test or reference product was evaluated by measuring the absorbance of the reaction media at 565 nm. For each concentration tested, the modulation of the collagenase and hyaluronidase enzymatic activities with the test product is calculated according to the following formula.

Percentage modulation of collagenase/hyaluronidase enzymatic activity=100×[(OD test or reference product−OD collagenase/hyaluronidase alone)/ OD collagenase/hyaluronidase alone]. [Math. 6]

If the result is negative, the percentage is expressed as enzyme inhibition; if the result is positive, the percentage is expressed as enzyme activation. The result for the metalloprotease inhibition is given below.

TABLE 11

|  |  | Inhibition versus control (%) |
| --- | --- | --- |
| *Peregrina* extract according to the invention | 1% | 87 |
|  | 0.5% | 87 |
|  | 0.1% | 88 |
|  | 0.01% | 62 |

Conclusion: The *peregrina* extract according to the invention gives rise to strong inhibition of metalloproteases (collagenase/hyaluronidase). It is capable of exerting 88% inhibition on these metalloproteases at and above a concentration of 0.1% and has good potential for protecting the extracellular matrix of the skin with great efficiency and, via this inhibition, it reveals an antiaging effect.

This is to be compared with the extract according to the Pierre Fabre patent FR 2 946 879, the results of which are given below according to the same test.

TABLE 12

|  |  | Inhibition versus control (%) |
| --- | --- | --- |
| *Moringa oleifera* extract according to the Pierre Fabre patent | 1% | Concentration not compatible with the test system |
|  | 0.5% | 4 |
|  | 0.1% | 24 |
|  | 0.01% | 42 |

Conclusion: the extract according to the Pierre Fabre patent shows a slight inverse-dose-dependent inhibitory action on collagenase activity with a peak inhibition of 42%, all concentrations combined, as opposed to a peak inhibition of 100% for the *peregrina* extract according to the invention.

The antiaging activity regarding this parameter appears to be different and novel in comparison with the effects observed with the extract according to the Pierre Fabre patent.

Example 12: Comparative Tests for the Antistress Activity (by Inhibition of PLA2)

For the antistress activity by inhibition of PLA2 on the skin, which affords a calmative/antistress orientation with an antiaging effect, two additional in tubo PLA2 tests were performed: one via the process according to the invention performed on *oleifera* cake (extract prepared identically to that on *peregrina* in the process according to the invention), one with the extract corresponding to the Pierre Fabre patent FR 2 946 879, another one corresponding to the BASF Beauty Care Solutions patent FR 3 076 460 with the product Purisoft® and finally a last one with the Chuun & Thurot patent FR2825267.

The object of this study is to evaluate the modulation of the antiinflammatory activity of the enzyme phospholipase A2 by one or more samples in an in vitro acellular model by means of the "SPLA2 (type V) Inhibitor Screening Assay Kit".

A buffered solution of phospholipase A2 reacts with a specific substrate, diheptanoyl thio-PC, and transforms it into a compound which binds to a chromogen, DTNB, with agitation at room temperature. The phospholipase A2 activity may thus be evaluated by measuring the absorbance at 413 nm.

The products "*peregrina* extract according to the invention" or the reference inhibitory product "thioetheramide-PC" are placed in contact with the phospholipase A2 solution at the same time as the enzyme substrate. The substrate transformed by the enzyme is stained by means of the chromogen DTNB by agitation at room temperature. The activity of phospholipase A2 in the presence/absence of the product "*peregrina* extract according to the invention" or of the reference product is then evaluated by measuring the absorbance at 413 nm.

The modulation of this activity is expressed as a percentage of inhibition or of activation of the phospholipase A2 activity in the absence of the active agent, i.e. only in the presence of the enzyme substrate (diheptanoyl thio-PC).

The inhibitor "thioetheramide-PC" at a concentration of 1 mg in 100 µl is the reference product (active control) in this study; said product inhibits the PLA2 activity by 93%, thus validating the test.

A solution of the enzyme phospholipase A2 is incubated in its substrate, diheptanoyl thio-PC, in the absence or presence of the reference inhibitor and of the test product "*peregrina* extract according to the invention", and the chromogen DTNB is then incorporated, followed by incubation for 15 minutes at 25° C.

At the end of the incubation period, the activity of the enzyme phospholipase A2 with and without the test or reference product was revealed by measuring the absorbance of the reaction media at 413 nm. For each concentration tested, the modulation of the phospholipase A2 enzymatic activity with the test product is calculated according to the following formula.

Percentage modulation of phospholipase A2 enzymatic activity=100×[(OD405 test product or reference product−OD405 sPLA2 alone)/OD405 sPLA2 alone]. [Math. 7]

If the result is negative, the percentage is expressed as enzyme inhibition; if the result is positive, the percentage is expressed as enzyme activation.

TABLE 13

| *Peregrina* extract according to the invention | 1% | 19 |
| --- | --- | --- |
|  | 0.1% | 16 |
|  | 0.01% | 11 |

The consistency and the substantially dose-dependent activity of this *peregrina* extract according to the invention on PLA2 inhibition reveal a calmative activity by reducing the intensity upstream of the arachidonic cascade. Such a calmative action far upstream of the arachidonic cascade reduces the impact of the basal physiological stress. The *peregrina* extract according to the invention is consequently an antistress agent.

With the protocol extract from the Pierre Fabre patent FR 2 946 879, the following results are obtained.

TABLE 14

| Pierre Fabre extract | 1% | 0 |
|---|---|---|
| | 0.1% | 16 |
| | 0.01% | 8 |

At 1%, which corresponds to its minimum working dosage, the extract does not show any activity. On dilution, activity appears, but the absence of a dose-dependent effect does not make it possible to validate a specific and reliable action of the extract on the inhibition of this enzyme.

With the protocol extract from the BASF Beauty Care Solutions patent FR 3 076 460 with the product Purisoft® LS9726, the following results are obtained.

TABLE 15

| BASF extract | 1% | 10 |
|---|---|---|
| Purisoft LS9726 | 0.1% | 12 |
| | 0.01% | 6 |

This extract shows a slight inhibitory action which does not reach the maximum amount observed at 1% with the *peregrina* extract according to the invention, i.e. 19% inhibition for the extract according to the invention as opposed to 10% inhibition at 1% for this extract.

With the protocol extract from the Chuun & Thurot patent FR 2 825 267, the following results are observed.

TABLE 16

| Chuun & Thurot extract | 1% | 0 |
|---|---|---|
| | 0.1% | 0 |
| | 0.01% | 0 |

This extract does not show any inhibitory action on this enzyme.

With the protocol extract from the process according to the present invention, but applied to the *Moringa oleifera* cake instead of the *Moringa peregrina* cake, the following results are observed.

TABLE 17

| *Moringa oleifera* extract | 1% | Not assayable |
|---|---|---|
| | 0.1% | 0 |
| | 0.01% | 6 |

This extract does not show any significant or stable inhibitory action on this enzyme.

Conclusion: only the *peregrina* extract according to the invention demonstrates significant inhibitory activity on the enzyme PLA2.

Example 13: Makeup Product Formulation

TABLE 18

| Ingredients | % |
|---|---|
| Water | qs |
| Caprylic/capric triglyceride | 19.0000 |
| Acacia senegal gum | 7.0000 |
| Charcoal | 6.0000 |
| Glycerol | 5.0000 |
| Propanediol | 5.0000 |
| Bentonite | 3.1500 |
| Cetearyl glucoside | 3.0000 |
| Cetearyl alcohol | 3.0000 |
| Benzyl alcohol | 1.0000 |
| *Peregrina* extract according to the invention | 2.0000 |
| Cellulose gum | 0.8000 |
| Xanthan gum | 0.1750 |
| Citric acid | 0.1750 |

Example 14: Washing Product Formulation

TABLE 19

| Ingredients | % |
|---|---|
| Water | qs |
| Sodium cocoyl sulfate | 5.0000 |
| Sodium cocoyl isethionate | 4.0000 |
| Bentonite | 3.7800 |
| Caprylic/capric triglyceride | 2.0000 |
| *Peregrina* extract according to the invention | 1.0000 |
| Gluconolactone | 0.7500 |
| Sodium benzoate | 0.5450 |
| Fragrance | 0.5000 |
| Xanthan gum | 0.2700 |
| Sodium stearoyl glutamate | 0.2250 |
| Citric acid | 0.2250 |
| Calcium gluconate | 0.0050 |

Example 15: Formulation of a Care Product (Antistress Antiaging Cream)

TABLE 20

| Ingredient | % |
|---|---|
| Water | qs |
| Caprylic/capric triglyceride | 18.0000 |
| Bentonite | 4.2000 |
| Cetearyl alcohol | 1.5000 |
| *Peregrina* extract according to the invention | 5.0000 |
| Gluconolactone | 0.7500 |
| Sodium benzoate | 0.5450 |
| Xanthan gum | 0.5000 |
| Fragrance | 0.5000 |
| Sodium stearoyl glutamate | 0.2500 |
| Citric acid | 0.2500 |
| Calcium gluconate | 0.0050 |

Example 16: Nutricosmetic Oral-Route Formulation

A 1 g tablet for calmative/antistress activity comprises: 3% dry extract according to the invention (containing 0.6% 2,5-diformylfuran on an inulin support)+47% calcium carbonate containing 200 IU vitamin D+25% magnesium gluconate+22% inulin+3% magnesium stearate.

Example 17: Toxicological Tests on the *Peregrina* Extract According to the Invention Preparation of the *Peregrina* Extract in Accordance with Example 1:

Seeds of *Moringa peregrina* (Forssk.) Fiori harvested when the fruit is ripe were dried to obtain an internal moisture content of about 6%, and then pressed with a mechanical endless screw press, so as to separate the oil from the rest of the seed in order to obtain, on the one hand, the virgin oil and, on the other hand, a cake. The cake is then isolated in the form of precut rolls in pieces of 1 to 2 cm. Maceration and extraction are performed on the cake with 96° ethanol preheated for 10 minutes at 55° C. in a ratio of 25%/75% (m/m). The mixture is sheared with a blender for 15 minutes and is then left to stir with by impeller for 2 hours at 20° C. The product is then filtered through a Büchner funnel under vacuum to obtain a pale yellow filtrate containing 1.15% dry matter. This filtrate is used in the tests that follow.

Determination of the Mutagenic Activity on the Bacterial Strain *Salmonella typhimurium* (TA 100)—Bacterial Reverse Mutation Test The test was conducted in three main phases:
- A preliminary experiment is performed in order to evaluate the cytotoxicity of the element to be tested and to select the dose range for the subsequent experiments,
- A first genotoxicity experiment (Test 1), with and without metabolic activation, with direct incorporation of the test system and the test (or of the controls) on minimal agar, on the dose range defined by the preliminary study,
- A second experiment (Test 2), with preincubation of the test system and of the test element (or of the controls), with and without metabolic activation, with dose levels defined by the study director after analysis of the results of the first experiment. This second experiment was performed in order to confirm or complete the results of the first one, in particular when equivocal or negative results were obtained. The dilutions of the test elements were prepared in analytical-grade water.

The cytotoxicity test was performed on the strain *Salmonella typhimurium* TA100 at concentrations of 5000, 1600, 500, 160 and 50 µg/plate, with and without S9-Mix.

The reagents used for preparing the S9-Mix were prepared according to the following instructions:

TABLE 21

| | Final concentration |
|---|---|
| MgCl$_2$ (0.4 M) + KCl (1.65 M) | 8 mM + 33 mM |
| Glucose 6-phosphate (0.2 M) | 5 mM |
| NADP (0.1 M) | 4 mM |
| Phosphate buffer for S9-Mix (pH 7.4-0.2 M) | 0.1 M |
| S9 fraction | 10% |
| Water | Adjust to final concentration |

The bacteria were exposed to the test extract with and without the metabolic activation system. The metabolic system used is a cofactor-supplemented post-mitochondrial fraction (S9). This S9 fraction, a microsomal fraction of Sprague-Dawley rat liver homogenate treated with an enzyme inducer, is prepared according to Maron, D. M. and Ames, B. N. (1983) and was supplied by Moltox T M. It is stored at a temperature below −70° C. The S9 microsomal fraction was used at a concentration of 10% in S9-Mix. The protocol applied was as follows:

The following were introduced into three hemolysis tubes:
assay without metabolic activation:
0.1 ml of the various concentrations of the test elements,
0.5 ml of sterile 0.2 M, pH 7.4 phosphate buffer,
2 ml of top agar for *S. typhimurium*,
0.1 ml of bacterial inoculum (TA100).
assay with metabolic activation:
0.1 ml of the various concentrations of the test elements,
2 ml of top agar for *S. typhimurium*,
0.1 ml of bacterial inoculum (TA100),
0.5 ml of S9-Mix.
Mix and pour onto the surface of the bottom agar previously spread in Petri dishes.
Incubate at 37° C.±2° C. for 48 to 72 hours.

These assays were performed for each test: preliminary cytotoxicity test, test 1 and test 2. The untreated control, the negative controls and the positive controls produced during the preincubation method were incubated for 20 to 30 minutes at 37° C.±2° C. before pouring the top agar.

The protocol applied was as follows:
Introduce the following into four 2-ml fractions of top agar for *S. typhimurium*:
0.1 ml of 0.2 M, pH 7.4 phosphate buffer,
0.1 ml of solvent,
0.1 ml of S9-Mix,
0.1 ml of the preparation of the test element at the highest concentration,
A 2 ml fraction of top agar for *S. typhimurium* is used to check its sterility.
Mix and pour onto the surface of the bottom agar previously spread in Petri dishes.
Incubate at 37° C.±2° C. for 48 to 72 hours.
The test is performed in triplicate.
No bacterial growth should be observed.

For at least five concentrations of the test extract, a test without metabolic activation and a test with metabolic activation were performed.

Expressing and Interpreting the Results

Many criteria make it possible to determine whether a result is positive, notably an increase in the number of revertants correlated to the dose of the test item, or a reproducible increase in the number of revertants at one or more concentrations, with or without metabolic activation.

The test element is considered to be mutagenic if, on conclusion of the verification steps, a dose-effect relationship was reproducibly obtained on one or more of the five strains with and/or without metabolic activation. Mutagenicity is only considered for a given concentration when the number of revertants is at least equal to twice the rate of spontaneous reversion for the strains TA98, TA100 and TA102 (R≥2) and three times the rate of spontaneous reversion for the strains TA1535 and TA1537 (R≥3).

The test element is considered to be non-mutagenic if, on conclusion of test 1 and test 2, the frequency of revertants always remained less than twice the rate of spontaneous reversion for all concentrations of the test element, for the strains TA98, TA100, and TA102 (R<2) and less than three times the rate of spontaneous reversion for the strains TA1535 and TA1537 (R<3), with and without metabolic activation, and provided that it was checked that the absence of the mutagenic effect was not related to the toxicity of the concentrations tested.

The preliminary study showed no cytotoxicity of the test element; consequently, this concentration range was used for the genotoxicity test 1.

On the basis of the result obtained for test 1, it was decided to use the same dilution range for test 2. The analysis of the revertants shows that:

No cytotoxic effect was observed,

No concentration of the test extract showed a ratio R greater than or equal to at least twice the rate of spontaneous reversion for TA98, TA100, and TA102 or three times the rate of spontaneous reversion for TA1535 and TA1537, with and without metabolic activation, No dose response was observed, irrespective of the test system or of the test conditions.

In the light of the results obtained in this study, the *peregrina* extract according to example 1 may be considered as having no mutagenic or promutagenic activity.

In Vitro Phototoxicity Test 3T3 NRU

The principle of the test is based on comparison of the cytotoxicity of the *peregrina* extract according to example 1 in the presence and absence of a non-cytotoxic dose of UVA, on cells in culture. The cytotoxicity is evaluated by determining cell viability using a vital stain: neutral red, 24 hours after treatment with the reference elements and the extract of *M. peregrina* with or without UVA irradiation. The cells used are mouse embryo fibroblasts of the Balb/c 3T3 clone 31 line (ATCC—CCL163). The positive control is a chlorpromazine solution (CAS No.: 69-09-0). The negative control is a diluent for the test extract and for the reference (buffered saline solution ±1% solvent). The *peregrina* extract was tested at eight concentrations in at least four culture wells per concentration studied, in the presence or absence of UVA. The fibroblasts were trypsinized, and two 96-well culture plates were seeded with 100 µl of a cell suspension containing $2 \times 10^5$ cells/ml (i.e., $2 \times 10^6$ cells per well) in complete culture medium.

The seeded plates were incubated for 24 hours at 37° C. and 5% $CO_2$. At the end of the incubation, semi-confluence of the cell lawn was checked. The dilutions were prepared just before being deposited on the cells. The pH of the highest concentration was measured; it was between 6.5 and 8. The culture medium was removed, each well was prerinsed cautiously with 150 µl of PBS maintained at room temperature and then treated with 100 µl of each extract or reference dilution. The culture plates were incubated in the dark for 1 h±5 minutes at 37° C. and 5% $CO_2$. Irradiation was performed using a Bio Sun solar irradiator (Vilber Lourmat RMX3W). The Bio Sun machine is a system which controls the UV irradiation by means of a programmable microprocessor. The system continuously follows the UV light emission. The irradiation stops automatically when the energy delivered is equal to the programmed energy. The spectral irradiance of the test device was measured in the wavelength range from 250 to 700 nanometers with a calibrated spectroradiometer. One of the two plates was irradiated with its cover on at room temperature, and the other plate was protected from UVA and was maintained at room temperature during the irradiation. After irradiation, the treatment medium was aspirated and the cells were rinsed. Without µl of complete culture medium were then added cautiously and the plates were incubated for 18 to 22 h at 37° C. and 5% $CO_2$. The next day, the cell viability (growth, morphology, monolayer integrity) was evaluated by observations using a phase-contrast microscope. The culture medium was removed, and each well was prerinsed and maintained at room temperature before being treated with 100 µl of the staining solution. The plates were returned to the incubator for 3 hours under the same conditions. The staining solution was removed and the cells were rinsed, the rinsing solution was then removed and 150 µl of desorption solution were added to each well. The plates were shaken until the crystals were fully dissolved. The absorbance values were measured at 450 nm.

Test Validation:

The UVA sensitivity of the cells is checked approximately every 10 passages by evaluation of their viability after exposing them to increasing irradiation doses. The cells are cultured at the density used in the test. They are irradiated the next day at a dose of 2.5 and 9 J/cm² and the cell viability is determined one day later by means of the NRU test. The cells meet the quality criteria if their viability after irradiation at 5 J/cm² of UVA is greater than or equal to 80% of the viability of the controls kept in the dark; at the highest dose of 9 J/cm² of UVA, the viability must be at least equal to 50% of that of the controls kept in the dark.

Results:

The negative control has an absorbance of greater than or equal to 0.4. Chlorpromazine, the positive control, has an $IC_{50}$ value of between 0.1 and 2 µg/ml in the presence of UVA and between 7 and 90 µg/ml in the absence of UVA. These results make it possible to validate the test. The concentration of the *peregrina* cake extract giving 50% cell death in the presence or absence of UVA cannot be estimated. The mortality never reached 50%. The concentration of the *peregrina* cake extract giving 50% cell viability in the presence or absence of UVA cannot be estimated. The viability is always greater than 50%.

Conclusion: Under the experimental conditions adopted, the *peregrina* cake extract may be considered as non-phototoxic.

Evaluation of the Ocular Irritant Potential by Study of the In Vitro Cytotoxicity Using the Neutral Red Release Method on the SI RC Cell Line This in vitro study is based on evaluation of the cytotoxicity of the *peregrina* cake extract by determining the concentration which results in 50% cell death ($IC_{50}$) on a cell monolayer by means of the neutral red release technique. The cells used are *mycoplasma*-free SIRC rabbit corneal fibroblasts (ATCC—CCL60).

The *peregrina* extract was diluted to 25% and 50% in physiological saline. The fibroblasts were trypsinized and two 24-well culture plates were seeded at a rate of 1 ml of a cell suspension containing $2 \times 10^5$ cells/ml in complete culture medium. The seeded plates were incubated overnight at 37° C. and 5% $CO_2$. At the end of the incubation, the confluence of the cell lawn was checked. The staining solution was prepared at 0.5 mg/ml in complete culture medium. The culture medium was removed and 1 ml of the staining solution was placed in each well. The plates were returned to the incubator at 37° C. and 5% $CO_2$ for 3 hours±15 minutes. After this contact time, the staining solution was removed and replaced with 1 ml of complete culture medium per well. The plates were maintained at room temperature for at least 30 minutes in order to stabilize the system before contact with the extract or the reference. Each well was rinsed with 2 ml of PBS, maintained at room temperature, and 500 µl of each dilution of *peregrina* extract or of reference were then placed in contact with the cell lawn. The contact time was 60 seconds (30 seconds for the positive control). The treatment was performed well by well with the stopwatch started at the moment that the *peregrina* extract or the reference was deposited. The plate was shaken manually throughout the treatment. After 55 seconds (or 25 seconds for the positive control), the dilution was aspirated. At precisely 60 or 30 seconds, five successive rinses were performed (5×2 ml PBS maintained at room temperature). The supernatant was aspirated after each rinse and after the final rinse the wells remained free of medium while awaiting the revelation phase. After complete treatment of the culture plate, 1 ml of the desorption solution was deposited in each well. The plate was shaken for about 15 minutes until homogeneous staining was obtained. The solutions obtained for each culture well were taken up and divided into two wells of a 96-well plate, i.e. 150 μl/well.

Results:

The concentration of the *peregrina* extract leading to 50% cell death was evaluated as >50%. The percentage of cell death at 50% of *peregrina* extract was evaluated as 17%.

Conclusion: Under the experimental conditions adopted, the cytotoxicity of the *peregrina* cake extract may be considered as being of negligible cytotoxicity.

Evaluation of the Skin Compatibility of a *Peregrina* Extract after a Single Application Under an Occlusive Dressing for 48 Hours Under Dermatological Control The aim of this study is to evaluate the degree of skin compatibility of the *peregrina* extract by epicutaneous test, performed on the antero-external face of the arm for 48 hours; and in general to evaluate the capacity of the *peregrina* extract to keep the skin in good condition. 10 healthy female or male volunteers, from 18 to 65 years old, having neither dry skin nor sensitive skin and free of any dermatological lesions on the treatment area were to be included in the study. The skin compatibility of the *peregrina* extract, prepared in the form of a lotion containing 5% of the *peregrina* extract according to example 1 and 95% of a propanediol/sorbitol mixture, was evaluated 48 hours after the initial application between 30 and 40 minutes after removing the dressing. The skin reactions (erythema and edema) were scored from 0 to 3 according to the following scales:

TABLE 22

| Score | Erythema (Er) | Edema (Ed) |
|---|---|---|
| 0 | no erythema | no edema |
| 0.5 | Barely perceptible erythema, very slightly pink coloring on part of the patched zone | palpable, barely perceptible edema |
| 1 | Mild erythema, pinkish coloring over the entire patched area | palpable and visible edema |
| 2 | Moderate erythema, clear coloring over the entire patched area | clear edema with or without papules or vesicles |
| 3 | Pronounced erythema, intense coloring over the entire patched zone | pronounced edema spreading outside the patched zone, with or without papules or vesicles |

Any other skin reactions (bullae, papules, vesicles, dryness, desquamation, roughness, soap effect, etc.) were evaluated according to the following scale and reported descriptively:

0: no reaction
0.5: very mild
1: mild
2: moderate
3: pronounced

At the end of the study, a mean irritation score (M.I.S.) was calculated according to the following formula:

$$\text{M.I.S.} = \text{sum of the skin reactions}(Er+Oe+bullae+papules+vesicles)/\text{Number of volunteers analyzed} \quad [\text{Math. 8}]$$

The M.I.S. obtained made it possible to classify the test extract according to the scale presented in the table below:

| | |
|---|---|
| M.I.S. ≤ 0.20 | Non-irritant |
| 0.20 < M.I.S. ≤ 0.50 | Slightly irritant |
| 0.50 < M.I.S. ≤ 2 | Moderately irritant |
| 2 < M.I.S. ≤ 3 | Highly irritant |

Results: The Mean Irritation Score (M.I.S.) for the *peregrina* cake extract is equal to: 0.

Conclusion: The *peregrina* cake extract may be considered as non-irritant after 48 consecutive hours of application on 12 volunteers.

General Conclusion of the Tests:

The results of the tests performed above are conclusive and demonstrate, for the *peregrina* extract according to example 1:

1) the eye and skin irritation tests are negative
2) the phototoxicity tests are negative
3) the mutagenicity tests are negative.

The safety of the *peregrina* extract according to the invention is demonstrated and ideal for large-scale topical cosmetic use without restriction as regards the target population.

Example 18: Evaluation by Measuring the Transepidermal Water Loss (TEWL) on the Skin Barrier and its Acceptability after Use Over a Period of 21 Days The product studied in this study is the care product in cream form of example 15. This product is applied morning and evening to the clean face by massaging gently, avoiding the area around the eyes. The measurements are taken on the cheeks.

The evaluation criteria are:
evaluation of the effect on the skin barrier: comparison of the TEWL values before any application of the product (D1) and then after 21 days of application (D21).
feedback on D21 regarding the discomfort sensations.
cosmetic acceptability: questionnaire filled in by the volunteer on D21.

22 female volunteers 50 years old on average (between 20 and 70 years old) with all skin types were tested. The product evaluated on the skin barrier gave the following results (*=% variation D21 relative to D1, **=Wilcoxon test for paired data with S=significant (p 0.05 and NS=non-significant (p>0.05):

TABLE 23

| | TEWL value (g/m² · h) | |
|---|---|---|
| | D1 | D21 |
| Mean | 11.70 | 11.79 |
| Standard deviation | 3.26 | 2.87 |
| Median | 10.39 | 11.40 |
| Minimum | 7.97 | 7.12 |
| Maximum | 17.30 | 17.14 |

TABLE 23-continued

| | TEWL value (g/m² · h) | |
|---|---|---|
| | D1 | D21 |
| % of variation* | — | 0.83 |
| Value of p** | — | p = 0.555 |
| Significance | | (NS) |

The analysis of the results shows that the TEWL remained stable at D21 in comparison with D1: the product showed a "dermo-protective" effect after 21 days of application. Given the absence of a significant reduction in the TEWL values at D21 in comparison with D1, the "nourishing" effect of the test product could not be revealed by instrumental measurements. 81% of the volunteers responded positively to the question "the skin is nourished" on the acceptability questionnaire at D21.

Conclusion: Under the conditions of the study, the cream showed a "dermo-protective" effect, revealed by TEWL measurement, and good cosmetic acceptability, with 86% of favorable opinions.

The invention claimed is:

1. A *Moringa peregrina* seed extract, obtained by a solid-liquid extraction of the unshelled seed cake, with stirring, in a proportion of about 25% by weight of solid matter relative to the total weight used in a predominantly alcoholic solvent, the alcohol being chosen from ethanol or methanol optionally with a cosolvent, in a proportion of from 70% to 100% by weight of alcohol relative to the total weight of the solvent, at a temperature of between 16 and 30° C. for a period of about 2 hours, and by separation of the liquid and solid phases so as to remove the solid phase and to recover a liquid extract of *Moringa peregrina* seed, said extract being rich in compound 2,5-diformylfuran.

2. The extract as claimed in claim 1, wherein the liquid extract obtained is dried so as to obtain a dry extract of the *Moringa peregrina* seed cake containing more than 50% by weight of 2,5-diformylfuran relative to the total weight of the dry matter.

3. A process for obtaining an extract of *Moringa peregrina* seeds as claimed in claim 1, comprising the following steps:
   a) collecting and drying unshelled seeds of *Moringa peregrina* to obtain an internal moisture content of less than 8%,
   b) pressing the dried seeds so as to separate the oil from the rest of the seed, to obtain the cake,
   c) milling the cake obtained in step b),
   d) dispersing the milled material obtained in step c), in a proportion of about 25% by weight of solid material relative to the total weight used, in a predominantly alcoholic solvent, the alcohol being chosen from ethanol or methanol optionally with a cosolvent, in a proportion of from 70% to 100% by weight of alcohol relative to the total weight of the solvent;
   e) performing a solid-liquid extraction, with stirring, at a temperature of between 16 and 30° C. over a period of about 2 hours,
   f) separating the liquid and solid phases so as to remove the solid phase and to recover a liquid *Moringa peregrina* cake extract, and
   g) optionally, when the alcohol is ethanol, drying the liquid *Moringa peregrina* extract obtained so as to obtain a solid *Moringa peregrina* extract.

4. The process as claimed in claim 3, wherein the predominantly alcoholic solvent is 96 degree pure ethanol.

5. The process as claimed in claim 3, wherein the liquid *Moringa peregrina* extract is purified by distillation, microfiltration, ultrafiltration and/or nanofiltration to concentrate the 2,5-diformylfuran of the extract relative to the organic materials also extracted.

6. A cosmetic or nutricosmetic composition comprising an active agent, an effective amount of an extract of *Moringa peregrina* seeds as claimed in claim 1, and a physiologically acceptable excipient.

7. The composition as claimed in claim 6, wherein a cosmetic composition formulated for topical application to the skin and in that the extract of *Moringa peregrina* seeds is present in the composition in a concentration of from 0.002% to 20% by weight, relative to the total weight of the composition.

8. The composition as claimed in claim 6, wherein a nutricosmetic composition formulated for ingestion and in that the extract of *Moringa peregrina* seeds is present in the composition in a concentration of from 0.01% to 100% by weight relative to the total weight of the composition.

9. The cosmetic or nutricosmetic composition as claimed in claim 6, for improving appearance of skin, mucous membranes or integuments, for relaxing, soothing and destressing the skin and for preventing and/or combating signs of aging and/or photoaging of the skin, and for preventing age spots.

* * * * *

UNITED STATES PATENT AND TRADEMARK OFFICE
CERTIFICATE OF CORRECTION

PATENT NO. : 11,717,476 B2
APPLICATION NO. : 17/633380
DATED : August 8, 2023
INVENTOR(S) : Dodinet et al.

It is certified that error appears in the above-identified patent and that said Letters Patent is hereby corrected as shown below:

On the Title Page

Item (71) Applicants: reads "AGENCE FRANAISE POUR LE DEVELOPPEMENT D'AL ULA, Paris (FR)" should read --AGENCE FRANCAISE POUR LE DEVELOPPEMENT D'AL ULA, Paris (FR)--

Item (73) Assignee: reads "AGENCE FRANAISE POUR LE DEVELOPPEMENT D'AL ULA, Paris (FR)" should read --AGENCE FRANCAISE POUR LE DEVELOPPEMENT D'AL ULA, Paris (FR)--

Signed and Sealed this
Twenty-fourth Day of October, 2023

Katherine Kelly Vidal
*Director of the United States Patent and Trademark Office*